United States Patent [19]

Schreiber

[11] Patent Number: 5,034,522
[45] Date of Patent: Jul. 23, 1991

[54] METHOD FOR THE PRODUCTION OF 3-METHYL CEPHEM DERIVATIVES

[75] Inventor: Fred G. Schreiber, Highland Park, N.J.

[73] Assignee: Biocraft Laboratories, Inc., Fairlawn, N.J.

[21] Appl. No.: 574,398

[22] Filed: Aug. 27, 1990

Related U.S. Application Data

[63] Continuation of Ser. No. 227,165, Aug. 2, 1988, abandoned.

[51] Int. Cl.$^5$ .............................. C07D 501/12
[52] U.S. Cl. ................................. 540/230; 540/215
[58] Field of Search ........................... 540/230, 215

[56] References Cited

U.S. PATENT DOCUMENTS

Re. 31,730 11/1984 Bouzard et al. .................. 540/230

Primary Examiner—Nicholas S. Rizzo
Attorney, Agent, or Firm—Bryan, Cave, McPheeters & McRoberts

[57] ABSTRACT

A method for obtaining improved cophalexin monohydrate or cephradine monohydrate yields and purities in the syntheses of such materials by the acylation of silyl esters of 7-ADCA, which involves admixing a cephalexin or cephradine-containing system with base to separate the acid acceptor employed during acylation from the product, and thereafter separating the aqueous phase containing the cephalosporin anion from the organin phase containing the acid acceptor, to thereby prevent contamination of the desired product by the acid acceptor.

16 Claims, 2 Drawing Sheets

METHOD FOR THE PRODUCTION OF 3-METHYL CEPHEM DERIVATIVES

This is a continuation of U.S. application Ser. No. 07/227,165 filed Aug. 2, 1988 now abandoned.

BACKGROUND OF THE INVENTION

1. Field of the Invention

The present invention relates to improvements in the synthesis of certain 3-methyl cephem derivatives, viz., cephalexin or cephradine, by the acylation of silyl esters of 7-ADCA. In particular, it relates to an improved recovery technique for obtaining such materials in good yields and purities.

2. Description of the Prior Art

Cephalexin and cephradine are antibacterial agents of the class of compounds commonly referred to as cephalosporins. Numerous disclosures of alternative methods for the production and purification of cephalexin and cephradine, their salts and hydrates, have appeared in the technical literature over the past twenty years.

In accordance with one commercially important synthesis, cephalexin or cephradine may be prepared by silylating 7-aminodesacetoxycephalosporanic acid (7-ADCA), reacting the resulting silyl ester with an appropriate acylating agent, cleaving the silyl protecting groups, and raising the pH of the reaction mixture to the isoelectric point to precipitate the desired product. Syntheses of this type are disclosed, for example, in British Patent No. 1,073,530; Japanese Patent Publication No. 41-3907 (1966); Weissenburger et al. U.S. Pat. Nos. 3,499,909 and 3,575,970; and Jackson U.S. Pat. Nos. 3,671,449 and 3,694,437. Similar procedures have also been proposed for the synthesis of the related 3-methyl cephem, cefadroxil; see, for example, Bouzard et al. U.S. Pat. No. 4,234,721 and Reissue Patent Re. 31730.

The acylation step in the cephalexin synthesis is conventionally carried out with an acylating agent comprising an N-protonated acyl halide of phenylglycine (or, in the case of cephradine, an N-protonated acyl halide of dihydrophenyl-glycine), e.g., alpha-phenylglycylchloride hydrochloride. During acylation with such materials, a strong protic acid, e.g., hydrogen chloride, forms as a by-product, impeding further reaction. It is thus necessary to carry out the acylation in the presence of an acid (HCl) acceptor, preferably a nitrogen base such as N,N'-dimethylaniline. Too strong an acid acceptor will strip the HX from the nitrogen of the acid halide and give by-products. Likewise, too weak an acid acceptor will not trap the HX formed.

Heretofore, the desired 3-methyl cephem products have been recovered by cleaving the silyl protective groups by hydrolysis or alcoholysis, and thereafter raising the pH of the resulting aqueous acidic solution to the isoelectric point to precipitate the cephalexin or cephradine. Unfortunately, the products thus recovered may be contaminated with the acid acceptor, e.g., the dimethylaniline, intimately combined with cephalexin or cephradine. To overcome this problem a variety of techniques have heretofore been proposed in an effort to avoid contamination by the organic acid acceptors, including very carefully controlled crystallizations, extensive washings, recrystallizations, etc.

It is among the objects of the present invention to provide an improved technique for recovering 3-methyl cephems synthesized by the acylation of silyl esters of 7-ADCA in the presence of an acid acceptor, by which technique the desired products may be recovered in good yields and purities, substantially free from contamination by the acid acceptor.

Other objects and advantages of the invention will appear from the following description of preferred embodiments thereof.

SUMMARY OF THE INVENTION

The present invention is directed to a technique for recovering certain 3-methyl cephems, viz., cephalexin or cephradine, which have been formed by silylating 7-ADCA, acylating the resulting silyl ester in a substantially anhydrous organic solvent medium in the presence of an acid acceptor, treating the acylation reaction mixture with water to quench the acylation reaction and cleave the silyl groups from the silyl ester, and adjusting the acidity of the aqueous phase thus formed to precipitate the desired 3-methyl cephem substantially free from contamination. In particular, the recovery technique of the invention involves:

(a) admixing the anhydrous reaction mixture, or the aqueous phase formed therefrom, with a strong base in an amount sufficient to effect removal of the acid acceptor into the organic solvent medium and simultaneously render the product soluble in the aqueous phase at pH 8–10;

(b) separating the aqueous phase from the organic phase, the latter containing the acid acceptor;

(c) extracting the aqueous phase with an organic extractant to remove substantially all of the organic impurities from the aqueous phase and leave 3-methyl cephem anion in substantially pure form;

(d) separating the second aqueous phase from the organic phase;

(e) carefully lowering the pH of the second aqueous phase to a pH of about 7.0–9.0 to initiate crystallization and give a slurry containing the 3-methyl cephem;

(f) lowering the pH of the slurry to about 4.5–5.0;

(g) cooling the slurry to about 0°–5° C.; and (h) separating the product thus precipitated from the slurry.

By thus proceeding, cephalexin monohydrate and cephradine monohydrate are produced in good yields and acceptable purities, substantially free from contamination by the acid acceptor.

BRIEF DESCRIPTION OF THE DRAWING

The attached drawing is a flow sheet illustrating preferred embodiments of the method of the present invention, wherein.

DETAILED DESCRIPTION OF THE INVENTION

Figure 1A:
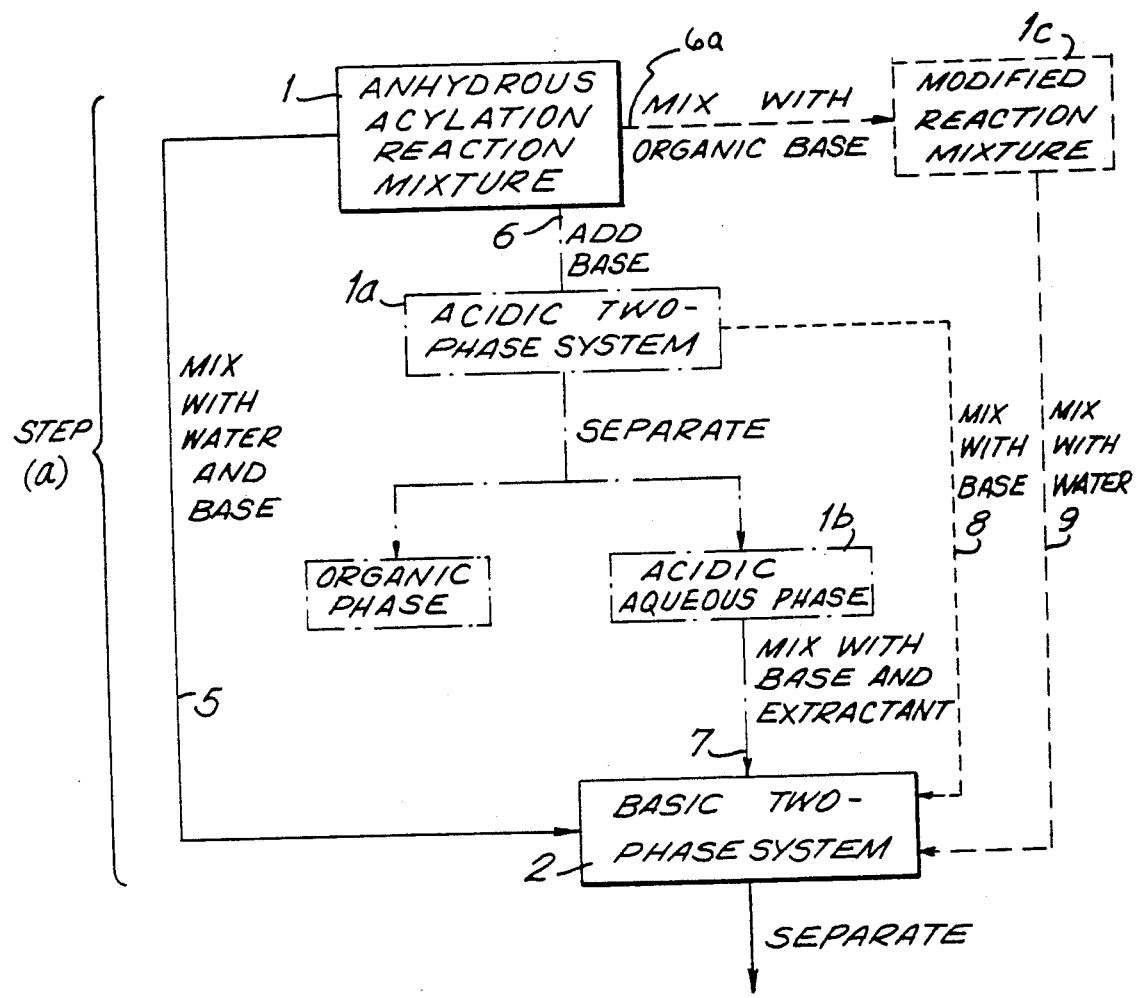
FIG. 1A illustrates step (a) thereof.
Figure 1B:
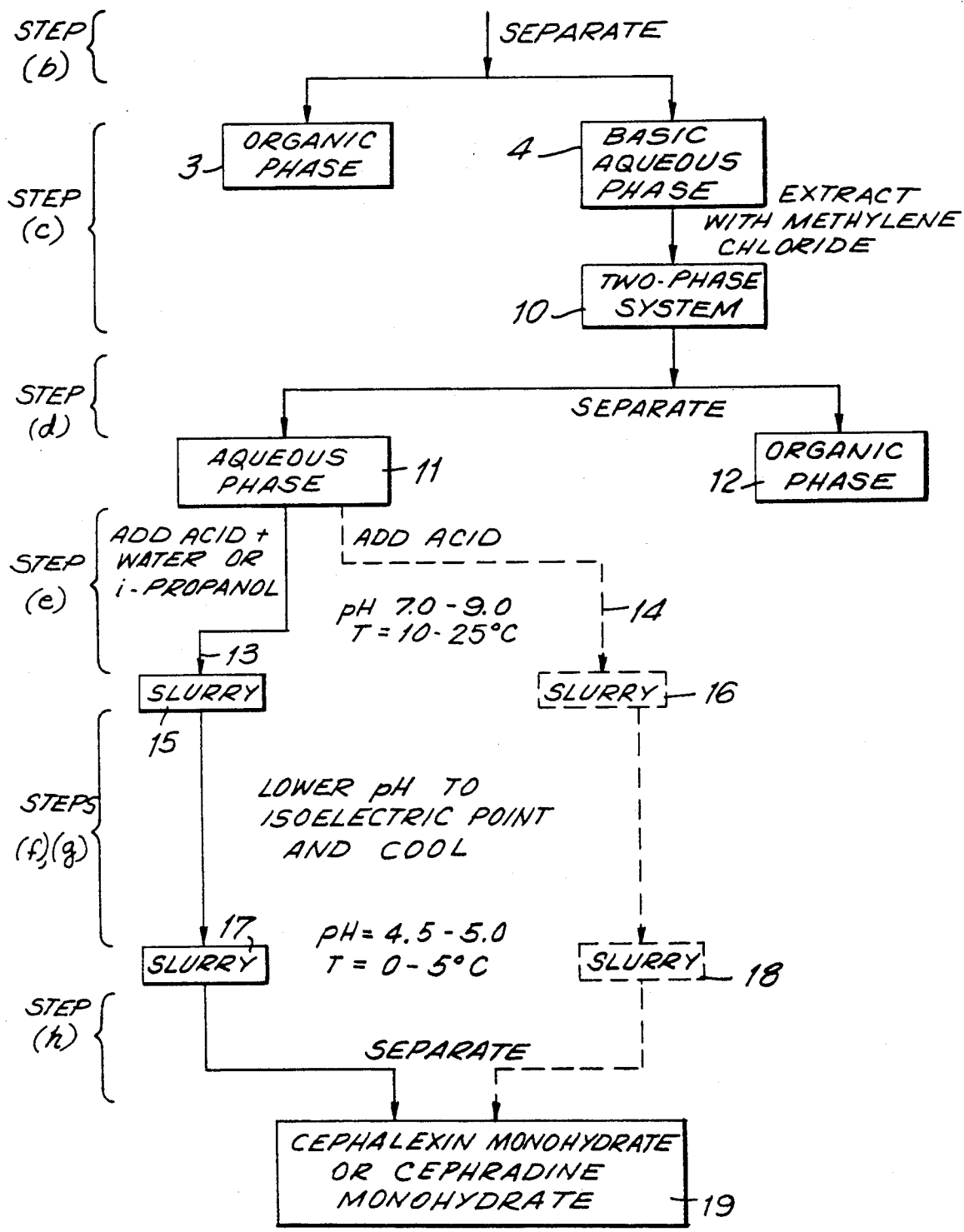
FIG. 1B illustrates steps (b)–(h) thereof.

Cephalexin monohydrate or cephradine monohydrate is produced in accordance with the present invention, employing the heretofore known synthesis commencing with the silylation of 7-ADCA in an inert, substantially anhydrous aprotic organic solvent. The silylation may be carried out in methylene chloride or other inert, substantially anhydrous organic solvent, such as disclosed in the aforesaid Bouzard et al. U.S. Reissue Patent, Re. 31,730, at col. 3, lines 9–13. Silylating agents useful in the method are known in the art and include those described or cross-referenced in both the aforesaid Bouzard et al. Re. 31,730 (col. 3, line 14-col. 4, line 3) and Jackson U.S. Pat. No. 3,694,437 (col. 2, line 28-col. 3, line 40). Silyl esters thus formed have the following formula:

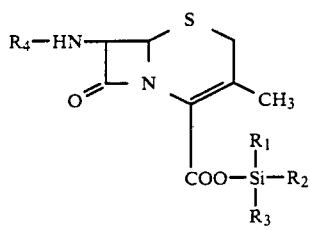

wherein $R_1$, $R_2$ and $R_3$ may each be hydrogen, halogen (lower) alkyl, halo (lower) alkyl, phenyl, benzyl, tolyl, or dimethylaminophenyl, and at least one of $R_1$, $R_2$ and $R_3$ is other than halogen or hydrogen; and $R_4$ is hydrogen or

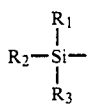

wherein $R_1$, $R_2$ and $R_3$ are as defined above.

As will be seen from the above formulae, the 7-ADCA reacts with 1 to 2 molar equivalents of the silylating agent to form the monosilylated ester, the disilylated ester, or mixtures thereof.

While any of the silylating agents incorporated by reference herein may be utilized in the synthesis, it is preferred to employ trimethylchlorosilane, or hexamethyldisilazane, or mixtures thereof, as the silylating agent. Utilizing these reagents, silyl esters having the following formula are produced:

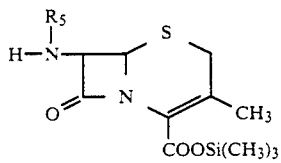

wherein $R_5$ is hydrogen or $Si(CH_3)_3$.

In accordance with the known synthesis, the silyl ester thus formed is then acylated employing a conventional N-protonated acid halide acylating agent such as an N-protonated phenyl-(or dihydrophenyl-) glycyl-halide hydrohalide, e.g., α-phenylglycyl-chloride hydrochloride and α-dihydrophenylglycylchloride hydrochloride. In the synthesis of cephalexin monohydrate it is preferred to use α-phenylglycylchloride hydrochloride as the acylating agent.

The acylation is preferably carried out in admixture with an acid acceptor, in the proportion of from about 1.00 to 1.25 moles per mole of the acylating agent, in an inert, substantially anhydrous aprotic solvent. The acid acceptor is suitably a relatively weak (i.e., $pK_a$ less than or equal to 7) tertiary amine base, preferably dimethylaniline. It traps the nascent hydrogen chloride in the acylation reaction mixture, permitting the acylation to go to completion. Preferably, methylene chloride is utilized as the solvent, although other inert organic solvents such as tetrahydrofuran, chloroform, tetrachloroethane, nitromethane, benzene, or diethyl ether may similarly be utilized.

The recovery procedure of this invention is designed to separate the acid acceptor from the desired 3-methyl cephem product, and thereby obviate contamination of the latter by the former. A description of a preferred embodiment of the recovery technique is described below in connection with the accompanying drawing. Referring to the drawing, the method involves recovery of the desired 3-methyl cephem product produced by hydrolysis of an anhydrous acylation reaction mixture 1, with the formation of a basic two-phase system 2. In accordance with the invention, the dimethylaniline acid acceptor which might otherwise contaminate the desired product is extracted into an organic phase 3 and separated from an aqueous phase 4 containing the desired 3-methyl cephem anion. The latter is further purified, as described below, to obtain the 3-methyl cephem product in high purity and yield.

The dimethylaniline acid acceptor is separated from the desired cephalosporin anion by an initial step (a), involving admixing either the anhydrous reaction mixture 1, or either an acidic two-phase system 1a or an acidic aqueous phase 1b derived therefrom, with a base in an amount sufficient to dissolve the product in the aqueous phase at the mildest possible pH of about 8-10, preferably about 9.0 to 9.5, to solubilize the dimethylaniline in the methylene chloride or other organic solvent. Preferably, the anhydrous reaction mixture is added to a stream 5 of water and the desired base, the water quenching the acylation reaction and cleaving the silyl groups from the silyl ester, leaving the desired 3-methyl cephem in the aqueous layer. By substantially simultaneously reacting the reaction mixture with base, the dimethylaniline is simultaneously extracted into the organic solvent, facilitating its subsequent separation. This preferred embodiment of the recovery technique of the present invention is exemplified in Examples 1,2 and 7-9 below.

Any conventional bases may be utilized to thus neutralize the acylation reaction mixture, including both organic amines such as triethylamine, trimethylamine, or pyridine, or inorganic bases such as the alkali metal or alkaline earth metal hydroxides or carbonates, ammonia gas or ammonium hydroxide solution. The use of sodium hydroxide or potassium hydroxide is preferred.

The acylation reaction mixture is desirably added to the water and base, rather than adding the water and base to the reaction mixture, since unmanageable pastes form in the latter instance which impair subsequent handling. Desirably, the reaction mixture is added to a dilute aqueous solution of the base. In order to maintain the desired mild pH 8-10 range, it may be necessary in large scale operations to add the reaction mixture and concentrated base, e.g., 25% NaOH solution, to water, either simultaneously or in alternating sequence. When the materials are mixed in alternating sequence, the pH of the reaction mixture is maintained within the necessary range throughout the mixing operation, i.e., the pH of the mixture fluctuates during mixing but is so regulated as to always be within the aforesaid range. If, on the other hand, the pH goes above 10 the product may be destroyed, and if the pH goes below 8 the product may precipitate prematurely.

Alternatively, as illustrated by stream 6 in the drawing, the reaction mixture 1 may be mixed with water alone to quench the mixture and effect the desired cleavage of the silyl ester groups. In this instance, the strongly acidic two phase system 1a containing both the 3-methyl cephem and the acid acceptor, or the acidic aqueous phase 1b remaining after separation of the acceptor-containing organic phase from the acidic system, is mixed with base at about pH 8-10 to produce the basic two-phase system 2. Operations in which the anhydrous acylation reaction mixture is first mixed with water and thereafter so basified are illustrated in Examples 3-5 below.

In yet a further alternative embodiment, the base, preferably an organic-miscible strong base, e.g., TEA or ammonia gas, may initially be added to the acylation reaction mixture, as shown by stream 6a in the drawing, to produce a modified reaction mixture 1c, and a water stream 9 thereafter mixed therewith to form the desired two-phase system 2. The initial addition of base to the anhydrous reaction mixture in such manner neutralizes the dimethylaniline-acid complex and thereby facilitates extraction of the dimethylaniline into the organic phase after water-quenching. This embodiment of the purification technique of the invention is exemplified in Example 6 below.

It will be noted that, unlike the preferred embodiment illustrated by stream 5 in the drawing, in the alternative embodiments illustrated by streams 6 and 9 the acylation reaction mixture may be mixed with the water streams by the addition of either mass to the other. This is possible since water quenching can be done without monitoring the pH, no unmanageable pastes are formed, and a two-phase liquid system is always obtained.

Whichever alternate technique is employed to carry out step (a) of the process, the total amount of water admixed with the acylation reaction mixture should range from about 60 to 170 moles per silyl ester equivalent to be hydrolyzed in the reaction mixture. With too little quenching water added, the large quantities of salt, e.g., NaCl and NH$_4$Cl formed in the quenching operation could make the aqueous phase nearly as dense as or denser than pure water leading to difficult separations from the organic layer. Reaction with the larger volumes of water within the noted range increases the rate of separation of the aqueous phase 4 from the organic phase 3 in the subsequent separation step (b). The use of larger water volumes also eliminates the need to add an organic solvent, such as isopropanol, in the subsequent crystallization step (e).

Accordingly, the determination of the specific proportions of water to be admixed with the reaction mixture in step (a) involves a compromise between the separation efficiency in step (b) and the yield of the ultimate product.

The organic and aqueous phases 3 and 4 are separated in step (b) by any suitable technique, e.g., by decantation, or other gravity separations, or the like. Greater than 99% of the dimethylaniline acid acceptor initially present is removed in the organic phase, and may be discarded or subjected to reprocessing. On the other hand, the basic aqueous phase 4 containing the desired 3-methyl cephem anions may be filtered, e.g., with charcoal, diatomaceous earth, or the like, and then subjected to further purification in steps (c)-(h).

In step (c) the aqueous phase 4 is further extracted with an appropriate extractant such as methylene chloride. Other solvents which are immiscible with water and in which the dimethylaniline or other acid acceptor is soluble may alternatively be used as extractants. Such solvents include methylisobutyl ketone, ethyl acetate, hexane, toluene, carbon tetrachloride or chloroform. The extractant is desirably utilized in an amount sufficient to extract substantially all of the remaining traces of the acid acceptor initially present.

The extraction step (c) yields a further two-phase system 10 comprising a further aqueous phase 11 containing the 3-methyl-cephem anions in substantially pure form, and a further organic phase 12 containing any residual dimethylaniline or other acid acceptor, silyl groups, or other organic solvent-soluble by-products. These phases are separated in step (d) by conventional operations, e.g., decantation or gravity separation, leaving the second aqueous phase for further purification.

It is within the scope of this invention to repeat the extraction and separation steps (c) and (d) one or more times to purify the desired 3-methyl cephem product, such repeated operations being identified as step (c') below. The final aqueous phase is then separated, acidified and cooled to precipitate the desired product, as described more fully below.

As further shown in the drawing, the pH of the second (or later) aqueous phase 11 is lowered in step (e) to a pH of about 7.0-9.0, preferably about 7.5-8.0, at a temperature of about 10°-25° C., preferably 15° to 20° C., to initiate crystallization of the 3-methyl cephem product. The temperature of the aqueous phase increases as the pH is lowered. It is, however, maintained within the specified range by cooling, if necessary. Too low a crystallization temperature will give tiny crystals that are very difficult to filter.

Desirably, the acidification is effected by adding stream 13 incorporating acid, e.g., HCl or H$_2$SO$_4$, and either isopropanol or additional water to the final aqueous phase. Alternatively, a stream 14 containing only acid may be added to initiate product precipitation. In both instances, slurries 15 and 16 begin to form at about pH 7.7. Seed crystals of the desired 3-methyl cephem, i.e., cephalexin monohydrate or cephradine monohydrate, may also be added to the second aqueous phase 11 to promote formation of the slurry.

The addition of more water or isopropanol to the acid stream increases both the rate and efficiency of the subsequent separation of the 3-methyl cephem product from slurry 15. The isopropanol, which is added in an amount of about 2-15 moles per mole of the 7-ADCA reacted, additionally removes colored impurities from the final products, thus further improving their purity. The addition of more water increases the volume of the mother liquor, improving the ultimate product purity. On the other hand, since cephalexin monohydrate and cephradine monohydrate are water soluble under certain conditions, the more water present in the slurry, the greater the potential for product loss. Desirably, from about 60 to 170 equivalents of water per equivalent of the 3-methyl cephem product should be added to the slurry in step (e).

Following initial precipitation, slurries 15 or 16 are further acidified and cooled in steps (f) and (g) to a pH of about 4.5-5.0 and a temperature of about 0°-5° C., effecting product precipitation in slurries 17 or 18, respectively. The acidification is preferably done before cooling so that better crystal growth occurs for rapid filtration rates.

Finally, as illustrated in step (h) of the accompanying flow sheet, slurries 17 or 18 are filtered or centrifuged to separate the desired cephalexin monohydrate or cephradine monohydrate products therefrom. The filter cake thus separated is washed with an organic solvent, e.g., isopropanol or acetone, and dried, e.g., in a vacuum or fluid bed dryer, to produce the final product in good yield and excellent purity.

The following specific examples further illustrate preferred embodiments for carrying out the method of the present invention. Unless otherwise indicated, in the examples as well as in the preceding general description all parts and percentages are given by weight and all temperatures in degrees Celsius.

EXAMPLE 1

Recovery of Cephalexin Monohydrate, Involving Addition of the Anhydrous Acylation Reaction Mixture to Water Plus Base A mixture of 403.36 g 7-ADCA, 170.80 g hexamethyldisilazane ("HMDS"), 108.23 g trimethylchlorosilane ("TMCS") and 3100 ml methylene chloride was stirred and refluxed for 2.5 hours to silylate the 7-ADCA. The mixture was cooled to 9° C. and 284.40 g dimethylaniline ("DMA") was added; the mixture was further cooled to 1° C., and 13.6 ml sulfuric acid was added. The mixture was recooled to 1° C., then 406.67 g alpha-phenylglycylchloride hydrochloride ("PGCH") was added with brine cooling. The mixture was stirred 30 minutes at 5° to 8° C. to acylate the silylated 7-ADCA, and then warmed to 25° to 27° C. for one hour.

The mixture was set aside overnight at room temperature. Analysis by thin layer chromatography showed almost complete acylation of the 7-ADCA.

The acylation reaction was quenched and DMA was liberated by feeding the mixture into 1430 ml water at 10° to 11° C. and pH 8.8 to 9.0. Simultaneously, 1029.73 grams of a sodium hydroxide solution (23.8% NaOH by weight) was added thereto. These three streams were combined over a period of 1.25 hours and a two phase system was formed [step (a)].

The two-phase system was stirred 15 minutes, then allowed to settle 30 minutes. The aqueous layer was treated with 5.4 g charcoal and 6.8 g Hyflo filter aid, and then filtered. The filtrate was extracted twice with 750 ml methylene chloride and refiltered [steps (c), (c') and (d)].

The final filtrate was diluted with 475 ml isopropyl alcohol ("IPA"), the pH was lowered to 7.4 by addition of concentrated HCl, and the mixture was seeded with cephalexin, to form a slurry [step (e)]. The pH was gradually lowered to 5.0 at 26° C. by the addition of 185.4 g concentrated HCl [step (f)], and the system was then cooled to 2° to 3° C. [step (g)].

The slurry was filtered to obtain a cephalexin monohydrate cake [step (h)], the cake was washed four times with 350 ml azeotropic IPA and acetone, and then dried.

The cephalexin monohydrate obtained by this method was very fluffy and snow-white.

| | |
|---|---|
| Yield: | 493.04 g (72%) |
| Moisture content (Karl Fischer): | 6.0% |
| Bulk density (after 1000 taps): | 0.358 g/ml |
| Potency (anhydrous basis): | 987 mcg/mg |
| DMA content: | 1.1 ppm |

EXAMPLE 2

Large Scale Recovery of Cephalexin Monohydrate, Involving Addition of the Anhydrous Acylation Reaction Mixture to Water Plus Base A mixture of 145.3 kg methylene chloride, 13,747 g 7-ADCA, 5839 g HMDS and 3704 g TMCS was refluxed in a 75 gallon reactor for 2.5 hours under nitrogen to silylate the 7-ADCA. The mixture was cooled to 6° C. and 9918 g DMA was added. The mixture was further cooled to −3° C. and 460 ml sulfuric acid was added. After the mixture was stirred for a short time, 13,826 g PGCH was added and the temperature was maintained at 5° to 8° C. to acylate the silylated 7-ADCA.

The mixture was stirred for 30 minutes, then warmed to 25° C. and stirred for an additional hour. Thereafter, the reaction mixture was cooled to 8° C. and added simultaneously with 25% caustic solution to 48.4 liters water (cooled to 2° C.) [step (a)]. During the mixing operation the reaction mixture was initially maintained at pH 9.0 to 10.0, and thereafter at pH 9.0 to 9.5. A two-phase system was thus formed.

A filter aid was added and the entire mixture was filtered. The organic and aqueous phases were separated [step (b)] and the aqueous phase was then extracted with successive portions of 25.4 kg methylene chloride [steps (c), (c') and (d)]. The aqueous layer was further treated with carbon and again filtered.

IPA (16 liters) was added to the aqueous phase and the pH was slowly lowered to 7.7 by acid addition [step (e)]. The system was seeded with cephalexin and, after crystallization began, the pH was lowered in 0.1 pH unit increments by acid addition to pH 7.0 [step (f)], and finally to pH 5.0 [step (h)]. The crystal slurry was chilled to 1° C. for 1 hour [step (g)], then centrifuged to obtain a cephalexin monohydrate product [step (h)].

The product was washed with IPA and acetone and then dried in a fluid bed dryer to yield:

| | |
|---|---|
| Cephalexin monohydrate: | 15.2 kg (65% yield) |
| Moisture content (KF): | 5.4% |
| Potency (anhydrous basis): | 962 mcg/mg |
| DMA: | 1.1 ppm |

EXAMPLE 3

Recovery of Cephalexin Monohydrate, Involving Mixing the Anhydrous Acylation Reaction Mixture With Water Alone, Separating the Aqueous Phase and Treating it with Base Plus Extractant 7-ADCA (47.17 grams) was silylated by refluxing with HMDS (19.65 grams) and TMCS (12.48 grams) in 435 ml. methylene chloride. The mixture was refluxed for 2.5 hours and then cooled to 0° C. DMA, 31.97 g, was added, the mixture was further cooled to 0° C., and then sulfuric acid (1 ml.) was added thereto. The silylated 7-ADCA mixture was then cooled to −15° C. and acylated by the addition of "PGCH" (47.43 grams). The mixture was stirred for 30 minutes at −5° C. and then warmed to 25° C. for 1 hour. Analysis by thin layer chromatography showed almost complete acylation of the 7-ADCA.

The system was chilled to −10° C. and 290 ml. water was added to quench the acylation reaction [step (a)]. A two-phase system was formed which comprised a strongly acidic aqueous phase containing both cephalexin and DMA, and an organic phase. The two phases were separated and the aqueous phase was added to a −10° C. solution of 132 ml. triethylamine ("TEA") and 70 ml. methylene chloride [step (c)]. The pH of the solution was 9.5 (at 3° C.) and the temperature was maintained at 0° C. to 5° C.

The aqueous layer was separated and re-extracted twice with separate 140 ml. portions of methylene chloride [steps (c'), (d)]

IPA (165 ml.) was added to the aqueous solution. Thereafter, the pH of the aqueous solution was reduced to pH 7.6 by the addition of hydrochloric acid, seed crystals were added, and the system was stirred until a slurry was formed [step (e)]. Increases in system pH due to crystallization of cephalexin monohydrate from the aqueous solution were corrected by the addition of HCl, thereby maintaining the system pH at 7.5.

After permitting the slurry to stand for 30 minutes, its pH was reduced to 5.0 by the addition of HCl [step (f)]. The system temperature rose to 24° C. as a result of this pH adjustment. The system temperature was then reduced to 2° C. for 30 minutes [step (g)]. A cephalexin monohydrate cake was obtained from the aqueous slurry by filtration [step (h)].

The cephalexin monohydrate cake was washed with azeotropic IPA and then acetone. Thereafter, the washed cephalexin monohydrate was dried in a vacuum oven at 45° C. for 1 hour. The product characteristics were:

| | |
|---|---|
| Cephalexin monohydrate yield: | 64.95 grams (81% yield) |
| Moisture content (Karl Fischer): | 7.4% |
| DMA content: | 0.5 ppm |
| Potency (anhydrous basis): | 1016 mcg/mg |

EXAMPLE 4

Recovery of Cephalexin Monohydrate, Involving Mixing the Anhydrous Acylation Reaction Mixture with Water Alone, Separating the Aqueous Phase, and Treating it with Base Plus Extractant Plus Water A mixture of 47.14 g 7-ADCA, 19.88 g HMDS, 12.64 g TMCS and 435 ml methylene chloride was refluxed for 2.5 hours to silylate the 7-ADCA. After cooling to 10° C., 32.81 g DMA was added. The mixture was cooled to 0° C. and 1.6 ml sulfuric acid was added. The mass was further cooled to −5° C., and then 47.50 g PGCH was added. The mixture was stirred 30 minutes at 5° to 10° C., then warmed to 26° to 27° C. for 1 hour to acylate the silylated 7-ADCA.

The mixture was cooled to −10° C., the acylation reaction was quenched with 185 ml water, and the system was stirred for 30 minutes at −5° C. A two-phase system was thus formed [step (a)]. The aqueous phase was separated therefrom, shaken with 0.75 g filtering agent, and filtered [step (b)].

The filtrate was added to a mixture of 132 ml TEA, 70 ml methylene chloride and 75 ml water at 0° C., to form a two-phase system having a pH of 9.2 at 2° C. [step (c)]. The aqueous phase was separated therefrom and extracted twice with 70 ml methylene chloride [steps (c') and (d)]. The resulting aqueous layer was treated with 0.75 g filtering aid and filtered. The pH was then lowered to 7.5 by the addition of concentrated HCl followed by seeding with cephalexin, thereby forming a slurry [step (e)]. The pH of the slurry was gradually lowered in 0.5 pH units to 5.0 at room temperature [step (f)]. The slurry was then chilled and filtered to obtain a cephalexin monohydrate cake [steps (g), and (h)].

The cake was washed with azeotropic IPA and acetone, then air dried to yield:

| | |
|---|---|
| Cephalexin monohydrate: | 64.20 g (80% yield) |
| Moisture content (KF): | 7.1% |
| DMA: | 0.7 ppm |

EXAMPLE 5

Recovery of Cephradine Monohydrate, Involving Mixing the Anhydrous Acylation Reaction Mixture With Water Alone, Then Treating the Aqueous Phase With Base 7-ADCA (30.10 grams) was silylated by refluxing with 12.30 grams HMDS and 8.21 grams TMCS in 275 ml. methylene chloride, for 2.5 hours. The mixture was cooled to 0° C. and 20.7 g, DMA and 1 ml. sulfuric acid were added sequentially to the system and mixed for 10 minutes. This mixture was chilled to −10° C. to −5° C. and 30.38 g dihydrophenylglycylchloride hydrochloride ("DHPGCH") were added. The system was maintained for 30 minutes to acylate the cephalosporin nucleus.

The acylation was quenched by the addition of 180 ml. water. The system was stirred for 30 minutes at 0° C. to 5° C. and a two-phase system was formed which comprised a strongly acidic aqueous solution of cephradine cation and DMA and an organic phase [step (a)]. The aqueous phase was separated from the organic phase and filtered with charcoal and diatomaceous earth [step (b)].

The filtered aqueous phase was added to a solution containing 80 ml. methylene chloride and 80 ml. TEA at a temperature of −10° C., thereby forming a two-phase system [step (c)]. The aqueous phase was separated from the organic phase, and re-extracted with methylene chloride [step (c')]. The final aqueous phase was separated from the organic phase [step (d)]. The aqueous phase was at a temperature of 10° C. and a pH of 9.2.

Hydrochloric acid was added to reduce the system pH to 8.5, at which point a thin slurry formed [step (e)]. The hydrochloric acid addition increased the system temperature. Further hydrochloric acid addition resulted in the crystallization of cephradine monohydrate as a thick slurry at pH 8.3 and at a temperature of 22° C. Thereafter, the slurry pH was slowly adjusted to 4.7 by further acid addition and the slurry was chilled to 5° C. [steps (f), (g)].

A cephradine monohydrate cake was obtained by filtering the slurry. The cake was washed with azeotropic IPA and air dried overnight. The product characteristics were:

| | |
|---|---|
| Cephradine monohydrate yield: | 34.7 grams (67% yield) |
| Cephalexin content: | 2.11% |
| Moisture content (Karl Fischer): | 4.4% by weight |
| DMA content: | 10.5 ppm |
| Potency: | 1013 mcg/mg |

EXAMPLE 6

Recovery of Cephalexin Monohydrate, Involving the Initial Addition of Base to the Anhydrous Acylation Reaction Mixture Prior to Phase Separation A mixture of 56.57 g 7-ADCA, 23.51 g HMDS, 15.19 g TMCS and 485 ml methylene chloride was refluxed for 2.5 hours to silylate the 7-ADCA. The mixture was cooled to 5° C. and 39.02 g DMA was added. The mixture was then further cooled to 0° C., and 1.9 ml sulfuric acid was added. PGCH (56.79 g) was then added and the mixture was stirred 30 minutes at 5° C. to acylate the silylated 7-ADCA. TEA (91 ml.) was then added while the temperature was maintained at −10° C. to −5° C.

The mixture was stirred for a short time, then diluted with 128 ml water to form a two-phase system, while allowing the temperature to increase to 8° C. [step (a)]. The system was stirred for 30 minutes and then separated [step (b)].

The aqueous phase was extracted with methylene chloride [step (c)]. The pH was maintained at 9.0 by adding TEA as necessary. The aqueous phase was then slowly treated with hydrochloric acid to pH 8.0 and seeded with cephalexin to form a slurry [step (e)]. After cephalexin monohydrate crystals appeared, the pH was slowly lowered to 5.0 and the slurry was cooled to 5° C. [steps (f), (g)]. The product was filtered to obtain a cephalexin monohydrate cake and the cake was washed with azeotropic IPA and acetone, then air dried to yield 63.36 g (66% yield) cephalexin monohydrate.

EXAMPLE 7

Increasing the Rate of Separation of Cephalexin Monohydrate by Increasing the Amount of Water To Which the Anhydrous Acylation Reaction Mixture is Added The general technique described in Examples 1 and 2 was repeated, modifying the amount of water to which the reaction mixture was added in the hydrolysis step to illustrate the effect on product yield and purity.

In a first experiment, a mixture of 79.73 g 7-ADCA, 34.41 g HMDS, 21.48 g TMCS and 610 ml methylene chloride was refluxed for 2.5 hours to silylate the 7-ADCA. The mixture was cooled to 10° C. and 57.61 g DMA was added. The mixture was further cooled to 0° C. and 2.7 ml sulfuric acid was added. 80.49 g PGCH was then added, keeping the temperature at 5° to 9° C. for 30 minutes to acylate the silylated 7-ADCA. The temperature of the system was raised to 20° C. and then allowed to exotherm to 25° to 30° C. for 1 hour. Thereafter, the mixture was set aside overnight.

The mixture was cooled to −5° C. and then added to 950 ml water (at 1° to 2° C.) and pH 8.2 to 9.2 with simultaneous addition of 199.3 g of 25% caustic solution to form a two-phase system [step (a)]. The water was thus present in an aggregate amount of 164 moles per equivalent of silyl ester. Filter aid (5 g) was added, the mixture was filtered and the filtrate was poured into a separatory funnel. Separation of the phases occurred in 4–5 minutes [step (b)].

The aqueous layer was twice extracted with 150 ml methylene chloride, treated with 3.15 g charcoal and filtered [steps (c) (c') and (d)]. The clear yellow filtrate was diluted with 95 ml IPA at a pH of 8.6 and a temperature of 15° C. [step (e)]. The pH was slowly lowered to 4.6 to produce well-defined cephalexin monohydrate needles [step (f)]. The mixture was chilled to 0° for 2 hours [step (g)] and filtered to obtain a cephalexin monohydrate cake [step (h)].

The cake was twice washed with 100 ml IPA and twice washed with 100 ml acetone. The product was air-dried overnight to yield:

| | |
|---|---|
| Cephalexin monohydrate: | 99.90 g (74% yield) |
| Moisture content (KF): | 5.5% |
| Potency: | 1001 mcg/mg |
| DMA: | 1 ppm |

EXAMPLE 8

Variation in Amount of Water Reacted in Example 7

The steps of Example 7 were repeated, except that the reaction mixture was added to 615 ml water (114 moles per equivalent of silyl ester) at 2° to 3° C. The process yielded:

| | |
|---|---|
| Cephalexin monohydrate: | 104.53 g (77% yield) |
| Melting Point (with decomposition): | 186° C. |
| Moisture Content (KF): | 5.5% |
| Potency: | 993 mcg/mg |
| DMA: | 1 ppm |

EXAMPLE 9

Omission of IPA from Crystallization Step of Example 7

The steps of Example 7 were repeated with 615 ml. water (7.72 ml water/g 7-ADCA or 114 moles of water per equivalent of silyl ester). The product was crystallized without IPA present. The process yielded:

| | |
|---|---|
| Cephalexin Monohydrate: | 101.65 g (75% yield) |
| Melting Point (with decomposition): | 191° C. |
| Moisture Content: | 5.4% |
| Potency: | 1007 mcg/mg |
| DMA: | 1 ppm |

It will be understood that the preceding examples illustrate preferred embodiments of the method of the present invention, without limiting the same. As noted above, various changes may be made in the sequence of the respective recovery operations without departing from the scope of the invention. These and other changes will be apparent to those versed in the art.

Having thus described the method of the invention, what is claimed is:

1. In a method for producing a 3-methyl cephem selected from the group consisting of cephalexin monohydrate and cephradine monohydrate, which comprises silylating 7-ADCA, acylating the resulting silyl ester in a substantially anhydrous, organic solvent medium in the presence of an acid acceptor comprising a tertiary amine base having a pKa no greater than 7, treating the acylation reaction mixture with water to quench the acylation reaction and cleave the silyl groups from the silyl ester, and adjusting the acidity of the aqueous phase thus formed to precipitate the 3-methyl cephem, the improvement which comprises:
   (a) admixing the anhydrous reaction mixture, or said aqueous phase, with a base in an amount sufficient to solubilize the acid acceptor in the organic solvent medium while simultaneously maintaining the 3-methyl cephem soluble in the aqueous phase at a pH of 8-10;
(b) separating the aqueous phase from the organic phase containing the acid acceptor;
(c) extracting the aqueous phase with an organic extractant to remove substantially all the organic impurities from the aqueous phase and leave a second aqueous phase containing the 3-methyl cephem anion in substantially pure form;
(d) separating the second aqueous phase from the resulting organic phase;
(e) adjusting the pH of the second aqueous phase to pH 7.0-9.0 to initiate crystallization;
(f) acidifying the slurry to pH 4.5-5.0;
(g) cooling the slurry to 0°-5° C.; and
(h) separating the 3-methyl cephem from the slurry.

2. The method of claim 1, for producing cephalexin monohydrate.

3. The method of claim 1, for producing cephradine monohydrate.

4. The method of claim 1, wherein the anhydrous acylation reaction mixture is admixed with base in step (a) by adding the reaction mixture to water and base to cleave the silyl groups from the silyl ester and substantially simultaneously solubilize the acid acceptor in the organic solvent medium and remove the acid acceptor from the aqueous phase containing the 3-methyl cephem thus formed.

5. The method of claim 1, wherein the aqueous phase is admixed with base in step (a) by mixing the reaction mixture with water to form a two-phase system, and the pH of the aqueous phase is raised above neutrality to maintain the 3-methyl cephem in solution.

6. The method of claim 1, wherein the aqueous phase is admixed with base in step (a) by mixing the reaction mixture with an organic base, and thereafter mixing the thus treated reaction mixture with water.

7. The method of claim 1, wherein the acid acceptor incorporated in the acylation reaction medium is dimethylaniline.

8. The method of claim 1, further comprising adding water or isopropanol to the second aqueous phase in step (e) in an amount effective to increase the speed and efficiency of precipitation of the 3-methyl cephem.

9. The method of claim 8, wherein isopropanol is added to the second aqueous phase in step (e) in an amount of from 2 to 15 equivalents per equivalent of 3-methyl cephem anion present therein.

10. The method of claim 1, wherein the 3-methyl cephem is separated in step (h) by filtering the slurry, washing the residual solids with a reagent selected from the group consisting of isopropyl alcohol and acetone, and drying.

11. In a method for producing a 3-methyl cephem selected from the group consisting of cephalexin monohydrate and cephradine monohydrate, which comprises
silylating 7-ADCA to produce a silyl ester having the formula:

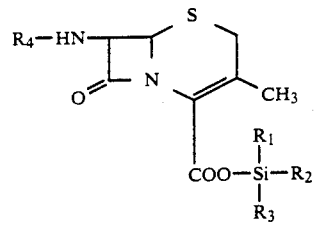

wherein
each of $R_1$, $R_2$ and $R_3$ is selected from the group consisting of hydrogen, halogen, lower alkyl, halo (lower) alkyl, phenyl, benzyl, tolyl or dimethylaminophenyl, and at least one $R_1$, $R_2$ and $R_3$ is other than halogen or hydrogen; and
$R_4$ is hydrogen or

acylating the resulting silyl ester with an N-protonated phenylglycine or dihydrophenylglycine acylating agent in a substantially anhydrous, organic solvent medium and in the presence of an acid acceptor comprising a tertiary amine base having a pKa no greater than 7;
treating the acylation reaction mixture with water to quench the acylation reaction and cleave the silyl groups from the silyl ester; and
adjusting the acidity of the aqueous phase thus formed to precipitate the 3-methyl cephem, the improvement which comprises:
(a) adding the anhydrous acylation reaction mixture to water and base in an amount sufficient to raise the pH of the resulting aqueous phase to pH 8-10, to cleave the silyl groups from the silyl ester while at the same time maintaining the 3-methyl cephem in the aqueous medium and substantially simultaneously solubilizing the acid acceptor in the organic solvent medium;
(b) separating the aqueous phase from the organic phase containing the acid acceptor;
(c) extracting the aqueous phase with an organic extractant to remove substantially all the organic-soluble impurities from the aqueous phase and leave a second aqueous phase containing the desired 3-methyl cephem anion in substantially pure form;
(c') repeating step (c) at least once to purify the 3-methyl cephem anion;
(d) separating the final aqueous phase from the organic phase admixed therewith;
(e) adjusting the pH of the final aqueous phase to pH 7.0-9.0 to initiate crystallization of the 3-methyl cephem;
(f) acidifying the slurry to pH 4.5-5.0;
(g) cooling the slurry to 0°-5° C.; and
(h) separating the 3-methyl cephem from the slurry.

12. The method of claim 11, for producing cephalexin monohydrate, wherein the acylating agent is an N-protonated phenylglycylhalide.

13. The method of claim 11, for producing cephradine monohydrate, wherein the acylating agent is an N-protonated dihydrophenylglycylhalide.

14. The method of claim 11, wherein the silylating agent is hexamethyldisilazane, trimethylchlorosilane, or a mixture thereof.

15. The method of claim 11, wherein the acid acceptor is dimethylaniline.

16. The method of claim 11, further comprising adding water or isopropanol to the final aqueous phase in step (e) in an amount effective to increase the speed and efficiency of precipitation of the 3-methyl cephem.

* * * * *